United States Patent
Modi

(10) Patent No.: US 6,294,153 B1
(45) Date of Patent: Sep. 25, 2001

(54) AEROSOL PHARMACEUTICAL FORMULATION FOR PULMONARY AND NASAL DELIVERY

(75) Inventor: Pankaj Modi, Ancaster (CA)

(73) Assignee: Generex Pharmaceuticals, Inc., Ontario (CA)

(*) Notice: Subject to any disclaimer, the term of this patent is extended or adjusted under 35 U.S.C. 154(b) by 0 days.

(21) Appl. No.: 09/397,102

(22) Filed: Sep. 16, 1999

Related U.S. Application Data

(60) Provisional application No. 60/113,243, filed on Dec. 21, 1998.

(51) Int. Cl.$^7$ ......................................... A61K 9/12
(52) U.S. Cl. ............................ 424/45; 424/46; 424/450; 424/184.1; 424/130.1; 424/198.1; 514/2
(58) Field of Search ..................... 424/45, 46, 450, 424/184.1, 130.1, 198.1; 514/2

(56) References Cited

U.S. PATENT DOCUMENTS

| | | |
|---|---|---|
| 4,579,730 | 4/1986 | Kidron et al. . |
| 4,582,820 | 4/1986 | Teng . |
| 4,839,111 * | 6/1989 | Huang . |
| 5,004,611 | 4/1991 | Leigh . |
| 5,006,343 | 4/1991 | Benson et al. . |
| 5,053,389 | 10/1991 | Balschmidt et al. . |
| 5,230,884 | 7/1993 | Evans et al. . |
| 5,288,497 | 2/1994 | Stanley et al. . |
| 5,306,483 * | 4/1994 | Mautone . |
| 5,653,987 | 8/1997 | Modi et al. . |
| 5,658,878 | 8/1997 | Bäckström et al. . |
| 5,672,581 | 9/1997 | Rubsamen et al. . |
| 5,676,931 | 10/1997 | Adjei et al. . |
| 5,690,954 | 11/1997 | Illum . |
| 5,747,445 | 5/1998 | Bäckström et al. . |
| 5,853,748 | 12/1998 | New . |
| 5,898,028 | 4/1999 | Jensen et al. . |
| 5,952,008 | 9/1999 | Bäckström et al. . |
| 5,985,309 | 11/1999 | Edwards et al. . |
| 6,017,545 * | 1/2000 | Modi . |
| 6,090,407 * | 7/2000 | Knight et al. . |

FOREIGN PATENT DOCUMENTS

| | | |
|---|---|---|
| 96/36352 | 11/1996 | (WO) . |
| 96/40057 | 12/1996 | (WO) . |
| 97/42938 | 11/1997 | (WO) . |
| 99/40932 | 8/1999 | (WO) . |

OTHER PUBLICATIONS

Kohler, D. (1993). Systemic Therapy with Aerosols. In: Aerosols in Medicine (Morén et al. eds), Elsevier Science Publishers, pp. 303–319.*

Patton et al. (1992). Advanced Drug Delivery Reviews, vol. 8, pp. 179–196.*

* cited by examiner

*Primary Examiner*—Raj Bawa
(74) *Attorney, Agent, or Firm*—Debra Z. Anderson; Eckert Seamens Cherin & Mellott, LLC

(57) ABSTRACT

An aerosol pharmaceutical formulation for pulmonary and nasal delivery is provided. The formulation comprises a pharmaceutical agent, water, a phenol and a propellant. Optionally, an excipient such as glycerin or polyglycerin, lysine or polylysine, or other salts, flavoring or coloring agents, protease inhibitors or stabilizers can be added. A method of administering the formulation with a metered dose dispenser, and a dispenser containing the formulation are also provided.

16 Claims, No Drawings

ID_ PHARMACEUTICAL FORMULATION FOR PULMONARY AND NASAL DELIVERY

This is a continuation of Application Ser. No. 60/113,243 filed Dec. 21, 1998.

FIELD OF THE INVENTION

The present invention relates to an improved delivery system for the administration of large-molecule pharmaceuticals, e.g. peptidic drugs, vaccines and hormones. In particular it relates to pharmaceuticals which may be administered by means of an aerosol into the mouth, for buccal or pulmonary application.

BACKGROUND TO THE INVENTION

For many years, attempts have been made to provide drug delivery technologies which are patient-friendly, non-invasive, and economically viable alternatives to injecting large macromolecule proteins. Some of the earliest efforts involved transdermal delivery via electroporations but this has mostly been abandoned because of technical difficulties in providing systems to carry large molecules through the skin. Oral delivery, which would clearly be the preferable dosage form, has had some success. However, a major obstacle is the degradation and denaturization of proteins in the gastrointestinal tract. The likelihood of the right amount of drug actually getting into the bloodstream reproducibly seems difficult even with the most advanced carrier technology. The lung appears advantageous because of the enormous surface area of the alveoli, and the fact that the lung can absorb both small and large molecules while simultaneously filtering out microparticle carriers and other unwanted toxins in the air. Large proteins, including antibodies, are readily absorbed through the alveoli either directly into the circulatory system or, more frequently, via the lymphatic system, which subsequently releases the drug into the bloodstream. Proteins in excess of 50 kilodaltons in molecular weight, which include the overwhelming majority of all biotech products on the market and in development, have been successfully delivered via the lung. No other non-invasive drug delivery system seems to have the potential to deliver large molecules as efficiently and quickly as pulmonary delivery through the lung.

Conventional metered dose inhalers, primarily used for asthma, deliver drugs into the upper branches of the lung. The ability to deliver drugs via small molecules through the deep lung and into the alveoli was one of the most significant technical breakthroughs in drug delivery. Conventional metered-dose inhalers (MDIs) deliver between 0–80% of the drug depending on the formulation and the propellant drug ratio.

In the current U.S. market for many drugs, improvements in drug delivery technology could have a significant impact. Rapid onset of action via non-injectable methods is an enormous opportunity. Pain management situations, e.g. breakthrough pain, post-surgical, migraine, and trauma/emergency room, represent a huge opportunity. New products are needed to address these drug delivery needs, while simultaneously providing patients with a convenient user friendly mechanism and physicians with a tool to improve overall diseases by improving therapy, compliance, and to prevent or reduce expensive hospital stays.

The terms "comprising" and "comprises" when used in this specification are taken to specify the presence of the stated features, integers, steps or components but do not preclude the presence or addition of one or more other features, integers, steps, components or groups thereof.

SUMMARY OF THE INVENTION

It has now been found that improvements in penetration and absorption of certain micellar formulations can be achieved by mixing the mixed micellar formulation with propellants such as tetrafluoroethane, heptafluoroethane, dimethylfluoropropane, tetrafluoropropane, butane, isobutane, dimethyl ether and other non-CFC and CFC propellants, especially when delivered (e.g. applied to the buccal mucosa) through aerosol devices, e.g. metered dose inhalers (MDIs). Metered dose inhalers are a proven technology and a popular drug delivery form for many kinds of drug. The use of the present novel formulations and excipients can improve the quality (in terms of absorption), stability and performance of MDI formulations. The formulation ingredients are selected specifically to give enhancement in the penetration through the pores and facilitate the absorption of the drugs to reach therapeutic levels in the plasma. With the proper formulation changes and changes in administration technique, the formulation can be delivered to the deep lungs, through the nasal cavity and the buccal cavity.

Pressurized inhalers also offer a wide dosing range, consistent dosing efficiency. In this local delivery greater than 95% of the dose is reached to the target area. The smaller particle size (4–15 microns) of pressurized inhalers also enhances dosing due to broader coverage within the lung cavity. In this situation, increased coverage can help more absorption of drug like insulin. Furthermore, because these devices are self-contained, the potential for contamination is avoided.

Accordingly the present invention provides an aerosol pharmaceutical formulation comprising i) a proteinic pharmaceutical agent, ii) water, iii) a phenol selected from the group consisting of phenol and methyl phenol in a concentration of from 1 to 10 wt./wt. % of the total formulation, and v) a propellant selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, and optionally iv) at least one excipient selected from the group consisting of salts, antioxidants, coloring agents, flavouring agents, protease inhibitors, stabilizers, glycerin, polyglycerin, lysine, polylysine and mixtures thereof.

In one embodiment, the proteinic pharmaceutical agent is in micellar form.

In another embodiment, the ratio of proteinic pharmaceutical agent, e.g. insulin, to propellant is from 5:95 to 25:75.

In a further embodiment, the methyl phenol is m-cresol.

In yet a further embodiment, the propellant is selected from the group consisting of tetrafluoroethane, tetrafluoropropane, dimethylfluoropropane, heptafluoropropane, dimethyl ether, n-butane and isobutane.

In yet another embodiment, the aerosol pharmaceutical formulation is contained in an aerosol dispenser.

The present invention also provides a metered dose aerosol dispenser with the aerosol pharmaceutical composition of the present invention therein.

The present invention also provides a method for administering an aerosol pharmaceutical compositions of the present invention, by spraying a predetermined amount of the composition into the mouth with a metered dose spray device.

The present invention also provides a method for administration of a proteinic pharmaceutical agent in a buccal cavity of a human being by spraying into the cavity, without inhalation, from a metered dose spray dispenser, a predetermined amount of an aerosol pharmaceutical formulation comprising i) a proteinic pharmaceutical agent, ii) water, iii) a phenol selected from the group consisting of phenol and methyl phenol in a concentration of from 1 to 10 wt./wt. % of the total formulation, and v) a propellant selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, and optionally iv) at least one excipient selected from the group consisting of salts, antioxidants, coloring agents, flavouring agents, protease inhibitors, stabilizers, glycerin, polyglycerin, lysine, polylysine and mixtures thereof.

DETAILED DESCRIPTION OF PREFERRED EMBODIMENTS

The present invention provides an improved method for delivery of macromolecular (high molecular weight) pharmaceutical agents, particularly through the membranes in the mouth or lungs. The pharmaceutical agents cover a wide spectrum of agents, including proteins, peptides, hormones, vaccines and drugs. The molecular weights of the macromolecular pharmaceutical agents are preferably above 1000, especially between 1000 and 2 000 000.

For example, preferred pharmaceutical agents include insulin, heparin, low molecular weight heparin, hirulog, hirugen, huridine, interferons, interleukins, cytokins, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), large molecule antibiotics, protein based thrombolytic compounds, platelet inhibitors, DNA, RNA, gene therapeutics, antisense oligonucleotides, opioids, narcotics, hypnotics, steroids and pain killers, e.g non-steroidal anti-inflammatory drugs.

As will be understood, the concentration of the pharmaceutical agent is an amount sufficient to be effective in treating or preventing a disorder or to regulate a physiological condition in an animal or human. The concentration or amount of pharmaceutical agent administered will depend on the parameters determined for the agent and the method of administration, e.g. nasal, pulmonary. For example, nasal formulations tend to require much lower concentrations of some ingredients in order to avoid irritation or burning of the nasal passages. It is sometimes desirable to dilute an oral formulation up to 10–100 times in order to provide a suitable nasal formulation.

The amount of physiologically peptide or protein in the compositions of this invention is typically a quantity that provides an effective amount of the drug to produce the physiological activity (therapeutic plasma level) for which peptide or protein is being administered. In consideration of the fact that the bioavailability of any active substance can never be 100%, that is to say the administered dose of the active drug is not completely absorbed, it is preferable to incorporate slightly larger amount than the desired dosage. Where the dosage form is a spray (aerosol) or the like which is repeatedly dispensed from the same container, it is recommandably so arranged that the unit dose will be slightly greater than the desired dose. It should be understood that dosage should vary with species of warm blood animals such as man, domestic animals, and their body weights.

The composition of this invention is preferably prepared as microfine micelles (1 to 10 nm or less) by the virtue of its preparation methods used. The utilization of atomizer or aerosol spray devices (metered dose inhalers or nebulizers) furthers a sufficient reduction of particle size for effective absorption from the nasal or lung cavity so the drug may successfully absorbed or reach to the specific site. The experience of the present inventor has shown a variety of proteins retain their biological activity even after prolonged exposure to MDI propellants.

For insulin-containing and some other compositions, the composition may also contains at least one inorganic salt which opens channels in the gastrointestinal tract and may provide additional stimulation to release insulin. Non-limiting examples of inorganic salts are sodium, potassium, calcium and zinc salts, especially sodium chloride, potassium chloride, calcium chloride, zinc chloride and sodium bicarbonate.

It will be recognized by those skilled in the art that for many pharmaceutical compositions it is usual to add at least one antioxidant to prevent degradation and oxidation of the pharmaceutically active ingredients. It will also be understood by those skilled in the art that colorants, flavouring agents and non-therapeutic amounts of other compounds may be included in the formulation. Typically flavouring agents are menthol and other fruit flavors.

The antioxidant is selected from the group consisting of tocopherol, deteroxime mesylate, methyl paraben, ethyl paraben and ascorbic acid and mixtures thereof. A preferred antioxidant is tocopherol.

In a preferred embodiment at least one protease inhibitor is added to the formulation to inhibit degradation of the pharmaceutical agent by the action of proteolytic enzymes. Of the known protease inhibitors, most are effective at concentrations of from 1 to 3 wt./wt. % of the formulation.

Non-limiting examples of effective protease inhibitors are bacitracin, soyabean trypsin, aprotinin and bacitracin derivatives, e.g. bacitracin methylene disalicylate. Bacitracin is the most effective of those named when used in concentrations of from 1.5 to 2 wt./wt. %. Soyabean trypsin and aprotinin two may be used in concentrations of about 1 to 2 wt./wt. % of the formulation.

It is believed that the phenolic compounds act mainly as preservatives and complexing agents to stabilize drugs, e.g. insulin. Besides their function as a stabilizer and preservative, they may also act as antiseptic agents and furthermore may help in absorption. The methyl phenol may be o-cresol, m-cresol or p-cresol, but m-cresol is preferred.

Typically, the aerosol pharmaceutical formulation is prepared by vigorously mixing the proteinic pharmaceutical agent, water, the phenol and the excipient so that at micellar formulation is formed.

After formation of the micellar formulation, the formulation is charged to a pressurizable container. Preferably the container is a vial suitable for use with a metered dose dispenser, e.g. a metered dose inhaler or applicator. Then the vial is charged with propellant. As the propellant is introduced into the vial, there is great turbulence in the vial and the propellant and pharmaceutical formulation become mixed. Some of the formulations with glycerin or polyglycerin in them tend not to separate on standing. Others may separate. For those aerosol formulations which are substantially homogeneous, it may not be necessary to shake the vial before use, although, through habit with other formulations, many users may shake the vial. Shaking the vial is recommended, however, in order to assure good accuracy of pharmaceutical dispensing from "shot" to "shot" and from the first shot to the last from the container. As is known, in order to deliver the pharmaceutical agent to the lung, it is necessary for the user to breathe deeply when the aerosol spray from the pressurized container is released. Without breathing in, the pharmaceutical agent is delivered to the buccal cavity. The method chosen will depend on a number of factors, including the type of pharmaceutical agent, the concentration in the aerosol, the desired rate of absorption required and the like.

A particular advantage with the use of metered dose dispensers is that the formulation can be delivered in a relatively precise dose, e.g. titratable to injection within 1 unit of insulin dose. The droplet size of the formulation preferably falls between 1–5 $\mu$m in order for droplets to penetrate buccal mucosa or to reach to the deep lung surface. Thus, the present invention is suitable for delivery of proteinic drugs such as insulin for the treatment of diabetes.

The pressurized dispensers also offer a wide dosing range and consistent dosing efficiency. With such a delivery, greater than about 95% of the dose may reach the target area. The smaller particle size (1–5 $\mu$m) obtained using pressurized inhalers also enhances dosing due to broader coverage within the lung cavity. In this situation, increased coverage can help more absorption of a drug like insulin. Furthermore, because these devices are self-contained, potential contamination is avoided.

Administration of the formulation into the buccal cavity is by spraying the formulation into the mouth, substantially without inhalation, so that the droplets stay in the mouth rather than be drawn into the lungs.

The advantages of the present invention are illustrated by the following non-limiting examples in which insulin is the pharmaceutical agent.

EXAMPLE 1

Appropriate quantity of insulin powder (in order to make 200 units, 400 units or 600 units per mL, depending on the activity (27.5–28.3 units/mg) was weighed accurately on an analytical balance. The powder was transferred to the glass beaker equipped with stirrer. Distilled water was added and the solution was stirred at low speed. To this was added 5M HCl (pH 2) solution dropwise till insulin powder was solubilized completely. This solution was then neutralized with 5M NaOH dropwise to pH 7–8. The solution was stirred continuously at low speed. To this solution was added glycerin or polyglycerin (10–20 mg/mL). The glycerin or polyglycerin was added to further enhance the absorption and also to make droplet size smaller within 1–5 microns for deep lung delivery. The solution was stirred further for 30 minutes and stored at 10° C. or at room temperature. This gave solutions containing insulin (200 U, 400 U or 600 U/mL). To these mixtures were added 15-mg phenol and 15 mg m-cresol dissolved in water to stabilize the formulation and protect against bacterial growth also to further enhance the absorption from oropharynx and trachea, from lungs and from the buccal cavity.

The solution of insulin (U200, or U400 or U600/mL) was pipetted (1 mL/vials) in glass vials coated outside with a plastic liners as the protective lining. The vials were then charged with a non-CFC tetrafluoroethane, (134a) propellant with the aid of a Pamasol 2008 semi-automatic gas filling equipment. The mount of propellant (HFA 134a) was adjusted to 9 mL hot size in order to deliver exact amount of insulin (2, 4 or 6 units/actuation) when actuated through the valve of the vial. The valves were designed to deliver 100 $\mu$L spray per actuation containing 2, 4 or 6 units insulin.

The aerodynamic particle size was determined by 8-stage USP Anderson Cascade Impactor-Mark-II (trade mark). The Multistage Cascade Impactor was cleaned with methanol and air-dried at 30° C. Glass fibre filters were placed on the collection plates. Seals were aligned properly and the actuator was attached to the mouthpiece and assembled onto the USP induction port and jet stages. A vacuum pump was connected and air flow rate is set to 28.3 liter/min. The vial was primed by shaking for 10 seconds and actuating twice to waste. The shot was delivered by discharging the actuator into the mouthpiece and repeated for 25 times. The deposited insulin was collected by rinsing the mouthpiece with 0.6 mg/mL EDTA in 10 mL water at pH 8.7. The filters were carefully removed and placed in scintillation vials and sonicated for 15 minutes. The quantity of the insulin was then analysed using RP-HPLC. Results:

| Stage # | vol. mL | mg | units | actuation | units/ Actuation | Particle size $\mu$m |
|---|---|---|---|---|---|---|
| 0 | 10 | | | | | |
| 1 | 10 | | | | | |
| 2 | 10 | | | | | |
| 3 | 10 | 0.77 | 10.1 | 5 | 2.0 | 4.0 |
| 4 | 10 | 0.78 | 10.1 | 5 | 2.0 | 3.8 |
| 5 | 10 | 0.81 | 10.0 | 5 | 2.0 | 3.0 |
| 6 | 10 | 0.80 | 10.3 | 5 | 2.0 | 2.1 |
| 7 | 10 | 0.80 | 10.1 | 5 | 2.0 | 1.0 |
| 8 | 10 | 0.79 | 10.1 | 5 | 2.0 | 0.7 |

(U400, 4 units/actuation)

| Stage # | vol. mL | mg | units | actuation | units/ Actuation | Particle size $\mu$m |
|---|---|---|---|---|---|---|
| 0 | 10 | | | | | |
| 1 | 10 | | | | | |
| 2 | 10 | | | | | |
| 3 | 10 | 0.77 | 20.1 | 5 | 4.0 | 3.8 |
| 4 | 10 | 0.78 | 20.1 | 5 | 4.0 | 3.3 |
| 5 | 10 | 0.81 | 20.0 | 5 | 4.0 | 3.0 |
| 6 | 10 | 0.80 | 20.3 | 5 | 4.0 | 2.0 |
| 7 | 10 | 0.80 | 20.1 | 5 | 4.0 | 1.0 |
| 8 | 10 | 0.79 | 20.1 | 5 | 4.0 | 0.6 |

Conclusion: The particle size was determined to be about 3 microns and stages 0–2 showed no insulin deposition indicating that most particles were smaller than 6 microns. Thus, this analysis indicates that there would be deep lung deposition, because the droplet size is generally smaller than 4 microns.

In addition, the shot size accuracy was determined by firing shots in a specially designed glass thiel tubes and weighing tubes before and after the sample collection.

For 4 units per Actuation: (Shot size accuracy determination) (U400), the results were:

| Shot Number | Shot Weight (g) |
|---|---|
| 10 | 0.078 |
| 15 | 0.083 |

-continued

| Shot Number | Shot Weight (g) |
|---|---|
| 20 | 0.076 |
| 25 | 0.079 |
| 30 | 0.070 |

For 6 units per Actuation: (Shot size accuracy determination) (U600), the results were:

| Shot Number | Shot Weight (g) |
|---|---|
| 10 | 0.17 |
| 20 | 0.18 |
| 30 | 0.182 |
| 40 | 0.174 |
| 70 | 0.177 |

Conclusion: The analysis indicates the uniformity of the shot size delivered through the valves.

Insulin Dose Delivered Volume (Units/Actuation) (HPLC Analysis):

The vial was primed by shaking for 10 seconds and actuating twice to waste. The shot was delivered by discharging the actuator into the mouthpiece and repeated for 25 times. The deposited insulin was collected by rinsing the mouthpiece with 0.6 mg/mL EDTA in 10 mL water at pH 8.7, carefully remove the filters and place them in scintillation vials and sonicate the vials for 15 minutes. The quantity of the insulin was then analysed using RP-HPLC. The procedure was repeated for 4 and 6 units/actuation formulation.

Insulin Dose Delivered Volume (Units/Actuation) (HPLC Analysis):

| Shot # | Peak Area (HPLC) | Dose ($\mu$g) | Dose (units) |
|---|---|---|---|
| 2 units/actuation | | | |
| (5–10) beg | 1796558 | 64.7 | 2.01 |
| (45–50) mid | 1679410 | 63.8 | 2.0 |
| (85–90) end | 1686757 | 65.0 | 2.06 |
| 4 units/actuation | | | |
| (5–10) beg | 2356780 | 118 | 4.2 |
| (45–50) mid | 2298510 | 110 | 4.0 |
| (85–90) end | 2199182 | 105 | 3.9 |
| 6 units/actuation | | | |
| (5–10) beg | 3017765 | 173.3 | 6.1 |
| (45–50) mid | 2984450 | 171.1 | 5.9 |
| (85–90) end | 3003560 | 172.7 | 6.0 |

Conclusion: The analysis indicates the uniformity of the dose delivered per actuation through the valves.

Clinical Results:

15 healthy volunteers were given the following doses of insulin for three days.

Day-1: 5 puffs of 2 units each (total 10 units)
Day-2: 5 puffs of 4 units each (total 20 units)
Day-1: 5 puffs of 6 units each (total 30 units)

Plasma insulin levels measured, in pmol/L, every 15 mins for first 90 mins and then every 30 mins for 2 hours.

| Time | Day-1 insulin 10 units | Day-2 insulin 20 units | Day-3 insulin 30 units |
|---|---|---|---|
| 0 | 35 | 38 | 42 |
| 15 | 56 | 62 | 72 |
| 30 | 89 | 97 | 112 |
| 45 | 119 | 138 | 178 |
| 60 | 160 | 178 | 202 |
| 75 | 160 | 175 | 190 |
| 90 | 142 | 157 | 173 |
| 120 | 78 | 112 | 141 |
| 150 | 62 | 87 | 92 |
| 180 | 37 | 49 | 67 |

These data shows significant absorption of insulin through lungs and oropharynx regions.

What is claimed is:

1. An aerosol pharmaceutical formulation for pulmonary or nasal delivery comprising i) a pharmaceutical agent, ii) water, iii) a phenol selected from the group consisting of phenol and methyl phenol is a concentration of from 1 to 10 wt./wt. % of the total formulation, and v) a propellant selected from the group consisting of C1–C2 dialkyl ether, butanes, fluorocarbon propellant, chlorofluorocarbon propellant, hydrogen-containing chlorofluorocarbon propellant, and mixtures thereof, and optionally iv) at least one excipient selected from the group consisting of salts, antioxidants, coloring agents, flavouring agents, protease inhibitors, stabilizers, glycerin, polyglycerin, lysine, polylysine and mixtures thereof.

2. An aerosol pharmaceutical formulation according to claim 1 wherein the pharmaceutical agent is in micellar form.

3. An aerosol pharmaceutical formulation according to claim 1 wherein the ratio of pharmaceutical agent to propellant is from 5:95 to 25:75.

4. An aerosol pharmaceutical formulation according to claim 1 wherein the methyl phenol is m-cresol.

5. An aerosol pharmaceutical formulation according to claim 1 wherein the propellant is selected from the group consisting of tetrafluoroethane, tetrafluoropropane, dimethylfluoropropane, heptafluoropropane, dimethyl ether, n-butane and isobutane.

6. An aerosol pharmaceutical formulation according to claim 1 wherein the pharmaceutical agent is selected from the group consisting of insulin, heparin, low molecular weight heparin, hirulog, hirugen, huridine, interferons, interleukins, cytokins, mono and polyclonal antibodies, immunoglobins, chemotherapeutic agents, vaccines, glycoproteins, bacterial toxins, hormones, calcitonins, insulin like growth factors (IGF), glucagon like peptides (GLP-1), antibiotics, thrombolytic compounds, platelet inhibitors, DNA, RNA, gene therapeutics and antisense oligonucleotides, opioids, narcotics, hypnotics, steroids, pain killers and non-steroidal anti-inflammatory drugs.

7. An aerosol pharmaceutical formulation according to claim 1 wherein the pharmaceutical agent is insulin.

8. A metered dose aerosol dispenser containing an aerosol pharmaceutical composition for pulmonary or nasal delivery comprising i) a pharmaceutical agent, ii) water, iii) phenol selected from the group consisting of phenol and methyl phenol in a concentration of from 1 to 10 wt./wt. % of the total formulation, and v) a propellant selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, and optionally iv) at least one excipient selected from the group consisting of salts, antioxidants, coloring agents, flavouring agents, protease inhibitors, stabilizers, glycerin, polyglycerin, lysine, polylysine and mixtures thereof.

9. A metered dose dispenser according to claim 8 wherein the ratio of pharmaceutical agent to propellant is from 5:95 to 25:75.

10. A metered dose dispenser according to claim 8 wherein the methyl phenol is m-cresol.

11. A metered dose dispenser according to claim 8 wherein the propellant is selected from the group consisting of tetrafluoroethane, tetrafluoropropane, dimethylfluoropropane, heptafluoropropane, dimethyl ether, n-butane and isobutane.

12. A metered dose dispenser according to claim 8 wherein the pharmaceutical agent is selected from the group consisting of insulin, heparin, low molecular weight heparin, hirulog, hirugen, huridine, interferons, interleukins, cytokins, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), antibiotics, thrombolytic compounds, platelet inhibitors, DNA, RNA, gene therapeutics and antisense oligonucleotides, opioids, narcotics, hypnotics, steroids, pain killers and non-steroidal anti-inflammatory drugs.

13. A metered dose dispenser according to claim 8 wherein the pharmaceutical agent is insulin.

14. A method for administering an aerosol pharmaceutical composition for pulmonary or nasal delivery comprising i) a pharmaceutical agent, ii) water, iii) a phenol selected from the group consisting of phenol and methyl phenol in a concentration of from 1 to 10 wt./wt. % of the total formulation, and v) a propellant selected from the group consisting of C1–C2 dialkyl ether, butanes, fluorocarbon propellant, hydrogen-containing fluorocarbon propellant, chlorofluorocarbon propellant, hydrogen-containing chlorofluorocarbon propellant, and mixtures thereof, and optionally iv) at least one excipient selected from the group consisting of salts, antioxidants, coloring agents, flavouring agents, protease inhibitors, stabilizers, glycerin, polyglycerin, lysine, polylysine and mixtures thereof, by spraying a predetermined amount of the composition into the nose or mouth with a metered dose spray device.

15. A method for administration of a pharmaceutical agent according to claim 14 wherein the pharmaceutical agent is selected from the group consisting of insulin, heparin, low molecular weight heparin, hirulog, hirugen, huridine, interferons, interleukins, cytokins, mono and polyclonal antibodies, immunoglobins, chemotherapeutic agents, vaccines, glycoproteins, bacterial toxoids, hormones, calcitonins, insulin like growth factors (IGF), glucagon like peptides (GLP-1), large molecule antibiotics, protein based thrombolytic compounds, platelet inhibitors, DNA, RNA, gene therapeutics and antisense oligonucleotides and many injectable opioids, narcotics, hypnotics, steroids, pain killers and non-steroidal anti-inflammatory drugs.

16. A method for administration of a pharmaceutical agent according to claim 14 wherein the pharmaceutical agent is insulin.

* * * * *